United States Patent [19]

Terada et al.

[11] 4,255,519
[45] Mar. 10, 1981

[54] GLYCEROL OXIDASE AND PROCESS FOR THE PRODUCTION THEREOF

[75] Inventors: Osamu Terada; Takayuki Uwajima, both of Machida; Hiroko Akita, Yokohama, all of Japan

[73] Assignee: Kyowa Hakko Kogyo Co., Ltd., Japan

[21] Appl. No.: 59,101

[22] Filed: Jul. 19, 1979

[30] Foreign Application Priority Data

Jul. 21, 1978 [JP] Japan .................................. 53/88261

[51] Int. Cl.³ .......................... C12N 9/04; G01N 31/14
[52] U.S. Cl. ....................................... 435/190; 435/25; 435/28; 435/933
[58] Field of Search .................. 435/190, 192, 933, 25, 435/27, 28

[56] References Cited

PUBLICATIONS

Journal of General Microbiology (1978), vol. 107, pp. 289-296.
Annual Review of Microbiology, vol. 30, pp. 535-578, (1976).

*Primary Examiner*—Lionel M. Shapiro
*Attorney, Agent, or Firm*—Craig & Antonelli

[57] ABSTRACT

Glycerol oxidase II is an oxidizing enzyme of glycerol characterized by its ability to oxidize glycerol in the presence of oxygen to form hydrogen peroxide and glyceraldehyde. This action of the present enzyme is the same as that of the enzyme glycerol oxidase I disclosed in U.S. application Ser. No. 897,695 filed on Apr. 19, 1978. However, this enzyme has characteristic properties in substrate specificity, optimum and stable pH, optimum temperature for action, substrate affinity (Michaelis constant glycerol). This enzyme is produced by culturing a microorganism belonging to the genus Penicillium.

7 Claims, 7 Drawing Figures

GLYCEROL OXIDASE AND PROCESS FOR THE PRODUCTION THEREOF

BACKGROUND OF THE INVENTION

This invention relates to an oxidizing enzyme of glycerol, which will be hereinafter referred to as "glycerol oxidase II", and a process for producing this oxidizing enzyme. Previously, the present inventors had found that there was a glycerol oxidase (now referred to as glycerol oxidase I) in the culture broth obtained by culturing microorganisms belonging to the genus Aspergillus or the genus Neurospora (U.S. application Ser. No. 897,695 filed on Apr. 19, 1978).

Afterwards, the present inventors have made further studies of another glycerol oxidase using microorganisms belonging to the genus Penicillium. As a result, we have found a fact that the present glycerol oxidase II has the same action as the glycerol oxidase (I) disclosed in the foregoing U.S. application, and also has other characteristic properties in substrate specificity, optimum and stable pH, optimum temperature for action, substrate affinity (Michaelis constant against glycerol).

SUMMARY OF THE INVENTION

In accordance with the present invention, glycerol oxidase II can be obtained by culturing a microorganism having an ability to produce an oxidizing enzyme of glycerol and belonging to the genus Penicillium in a nutrient medium containing an appropriate carbon source, nitrogen source, inorganic material and other nutrients, and recovering glycerol oxidase II from the resulting culture broth.

Any microorganism belonging to the genus Penicillium can be used, so long as it has an ability to produce glycerol oxidase II. As suitable microorganisms, Penicillium sp. KY 868 (FERM-P 4567, NRRL 11339) can be mentioned.

DETAILED DESCRIPTION OF THE INVENTION

The enzyme provided according to the process of the present invention has the following enzymological and physicochemical properties:

(a) Action:

The present glycerol oxidase oxidizes glycerol under the consumption of oxygen to form hydrogen peroxide and glyceraldehyde.

(b) Substrate specificity:

The present enzyme reacts specifically with glycerol and dihydroxyacetone.

(c) Optimum pH: 7.8–8.6

(d) Stable pH: 7.5–10.0

(e) Optimum temperature for action: 37° C.

(f) Michaelis constant against glycerol (Km value): $8.0 \times 10^{-3}$ M (g) Condition for Inactivation by pH:

Glycerol oxidase II is inactivated at pH value of above 10.5 or below 7.0 for 30 minutes.

(h) Condition for Inactivation by temperature:

Glycerol oxidase II is inactivated about 15% after treatment at 45° C. for 30 minutes and about 65% after treatment at 50° C. for 30 minutes.

(i) Inhibitors of enzyme:

Enzymes activities obtained by adding 1 mM of various inhibitors are shown in Table 1, the activity of the enzyme with no addition of the inhibitor being defined as 100. The activities are calculated from consumption rate of oxygen used in reaction measured by Warburg's manometer.

TABLE 1

| Inhibitor | Relative rate (%) |
|---|---|
| None | 100 |
| $AgNO_3$ | 0 |
| $HgCl_2$ | 79.0 |
| $Pb(CH_3COO)_2$ | 26.3 |
| p-Chloromercuri benzoate | 81.4 |
| $ZnCl_2$ | 84.3 |
| $FeSO_4$ | 0 |
| $NH_2OH$ | 0 |
| o-Phenanthroline | 65.5 |
| $\alpha,\alpha'$-Dipyridyl | 75.7 |
| EDTA | 82.8 |
| Neocuproine | 80.3 |
| Diethyl dithiocarbamate | 0 |

(j) Stabilization of enzyme:

Heat-resistance and preservation-stability of enzyme are improved by using Good's TES[N-tris(hydroxymethyl)methyl-2-amino-ethanesulfonic acid] buffer (Biochemistry, 5, No. 2, 467–477, 1966).

(k) Molecular weight:

The molecular weight of glycerol oxidase II is presumed as 300,000 or more according to the elution pattern by analysis using Sephadex G-200 column.

(l) Crystal structure and elemental analysis:

No crystallization has been succeeded yet, and no determination has been made yet.

Now, Penicillium sp. KY 868 used in the present invention has the following morphological characteristic.

1. Culture characteristics on various media:
   (a) Colonies on Czapek's solution agar growing very poorly, attaining a diameter of about 15 mm in a week, thin and semitransparent.
   (b) Colonies on malt extract agar growing to about 32 mm in diameter, flat and compact, margin white, conidial area olive (1½ni−1½pl, Color Harmony Manual; Container Corp. of America), no exudate, reverse white.

2. Conidiophores growing to about 50μ in length and 3μ in diameter, branching once or twice asymmetrically (Asymmetrica), with walls something granular.

3. Metulae strongly divergent (Divaricata), about 9 to 12μ by 2.5 to 3μ, with walls granular.
4. Sterigmata about 8 to 9μ by 2.5 to 3μ narrowing and inflating to apices forming bowling pin-shape.
5. Conidia about 3μ in diameter, definitely echinulate but not conspicuous.
6. Sclerotia and perithecia: None
7. Growth temperature:
   On malt extract agar, growing moderately at 25° C. and sporulating abundantly, but at 30° C. growing completely restrictedly without sporulation.
8. Nutritional requirement:
   On Czapek's solution agar at 25° C., growing very poorly (1−(a)), but on steep agar growing larger and thicker sporulating abundantly, and growing much better on malt extract agar.
9. Physiological conditions
   (a) Optimum growth condition
   pH:4–7, temperature:20°–25° C.
   (b) Growth range
   pH:2–9, temperature:0°–30° C.

According to *A Manual of the Penicilla*, K. B. Raper, C. Thom, D. I. Fennel (The Williams & Wilkins Company, Baltimore), it is evident that the Penicillium sp. having the foregoing morphological characteristic is a fungi belonging to *Penicillium nigricans* series. But, the accurate position of the fungi was not yet determined from the literature.

Now, in the present invention, any microorganism can be used, so long as it belongs to the genus Penicillium and has an ability to produce glycerol oxidase II. As suitable microorganisms, Penicillium sp. KY 868 (FERM-P 4567, NRRL 11339) can be mentioned.

Any of synthetic medium and natural medium can be used as a medium in the present invention, so long as it properly contains a carbon source, nitrogen source, inorganic materials and other nutrients.

As the carbon source, carbohydrates such as glucose, sucrose, blackstrap molasses, etc. and sugar alcohols such as glycerol, sorbitol, mannitol, etc. can be used.

As the nitrogen source, aqueous ammonia, various inorganic and organic ammonium compounds such as ammonium chloride, ammonium sulfate, ammonium carbonate, ammonium phosphate, etc., nitrogen compounds such as urea, etc., nitrogenous organic materials such as peptone, yeast extract, casein hydrolyzate, defatted soybeans, or the digested products thereof, etc., can be used.

As the inorganic materials, salts of metals such as sodium, potassium, manganese, magnesium, calcium, cobalt, nickel, zinc, copper, etc., and salts of chromium, sulfuric acid, phosphoric acid, nitric acid, hydrochloric acid, etc., can be used.

In the present invention, glycerol oxidase II can be obtained in best yield when a glycerol oxidase II-producing microorganism is cultured in a medium containing glycerol.

Culturing is usually carried out at a temperature of 18° to 30° C., preferably 20° to 35° C. and at a pH of 6 to 8 at the start of culturing, preferably at about 6.5. A considerable amount of glycerol oxidase II is formed in the resulting culture broth by shaking culture or aeration-agitation submerged culture under said conditions for 30 to 72 hours.

Glycerol oxidase II thus formed in the resulting culture broth can be recovered in the following manner:

Since glycerol oxidase II is usually formed in the microbial cells, the procedure for recovering the enzyme from the microbial cells is described below.

After the completion of culturing, microbial cells obtained by filtration of culture broth are sufficiently washed with water or buffer solution. Then, the microbial cells are suspended in an appropriate amount of a buffer solution, and disrupted. Disruption is carried out by mechanical disintegration (for example, by mortar, Dyno-mill, Manton goulin, French press, Fuse press, ultrasonic disintegrator, etc.).

Solid materials are removed from the resulting solution of the disrupted microbial cells by filtration or centrifugation, and then glycerol oxidase II is recovered from the solution according to the conventional procedure for isolating enzymes. For example, enzyme powders can be obtained according to steps of (1) fractional precipitation with ammonium sulfate, (2) column chromatography on DEAE cellulose, (3) sieve fractionation by Sephadex, (4) column chromatography on hydroxyapatite, and (5) freeze-drying of active fractions. Of course, repetition of the same operating steps, and other conventional purification methods can be used in combination, if required.

Enzymological and physicochemical properties of glycerol oxidase (II) obtained are described in detail below (as glycerol oxidase II, the purified preparate obtained in Example 1 is used).

I. Action

The present glycerol oxidase II oxidizes glycerol under the consumption of oxygen to form hydrogen peroxide and glyceraldehyde.

(a) Confirmation of formation of hydrogen peroxide:

(a)-1. Glycerol oxidase II is reacted with glycerol in the presence of oxygen, and then peroxidase, phenol and 4-aminoantipyrine are added to the enzyme system, whereby quinoneimine pigment is formed in the reaction system [reaction of hydrogen peroxide with peroxidase, phenol and 4-amino-antipyrine is disclosed in Clin. Chem. 20, p. 470 (1974)].

(a)-2. Glycerol oxidase is reacted with glycerol in the presence of oxygen to form hydrogen peroxide, and catalase is added to decompose the generated hydrogen peroxide. Then, peroxidase, phenol and 4-amino-antipyrine are added to the reaction system to conduct the same reaction as above, but the same quinoneimine pigment is not formed in the reaction system.

(a)-3. When catalase is presented in the glycerol oxidation system catalyzed by glycerol oxidase in the presence of oxygen, the amount of oxygen uptake is decreased to half. This fact is supported by the following experimental facts:

(a)-3-1. Reaction Composition A (system free from catalase);

| Reagents | |
|---|---|
| Aqueous 0.01M glycerol solution | 0.5 ml |
| 0.1M TES buffer solution (pH 8.0) | 1.0 ml |
| Aqueous glycerol oxidase solution | 0.2 ml[*1] |
| Aqueous 2.4 mM 4-amino-antipyrine solution | 0.5 ml |
| Aqueous 42 mM phenol solution | 0.5 ml |
| Aqueous peroxidase solution | 0.2 ml[*2] |
| Water | 0.1 ml |

[*1]Containing 5 μ moles of glycerol oxidase having a specific activity of 6.3 obtained in Example 1 of the present invention.
[*2]Made by Sigma Corp. (U.S.A.), containing 200 units of specific activity of 1,000.

(a)-3-2. Reaction Composition B (system containing catalase):

| Reagents | |
|---|---|
| Aqueous 0.01M glycerol solution | 0.5 ml |
| 0.1M TES buffer solution (pH 8.0) | 1.0 ml |
| Aqueous glycerol oxidase solution | 0.2 ml*¹ |
| Aqueous catalase solution | 1.0 ml*³ |
| Water | 0.3 ml |

*¹Same as in Reaction Composition A.
*³Made by Sigma Corp. (U.S.A.), containing 100 units of catalase having specific activity of 100.

Figure 1:
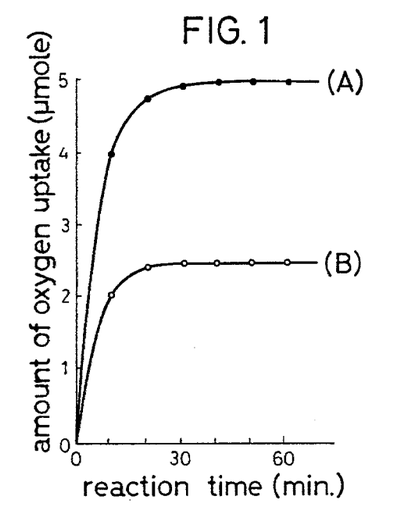
FIG. 1 shows the amount of oxygen uptake in a reaction system where glycerol oxidase II is reacted with glycerol in the presence of oxygen. In this figure, curve A represents the amount of the oxygen uptake in the reaction system free from catalase and curve B the amount of the oxygen uptake in the presence of catalase.

(a)-3-3. Reaction operation:

In case of the system free from catalase, the reagents shown in Reaction Composition A are mixed, and reaction is carried out at 37° C. with stirring. The amount of oxygen uptake is measured by Warburg's manometer. The results are shown in FIG. 1.

In case of the system containing catalase, the reagents shown in Reaction Composition B are mixed, and reaction is carried out at 37° C. Similarly, the amount of oxygen uptake is measured, and is shown in FIG. 1. As is evident from FIG. 1, 4.98 μ moles of oxygen is consumed in the absence of catalase (curve A in FIG. 1) for 5.0 μ moles of glycerol as a substrate.

In the presence of catalase (curve B in FIG. 1), 2.51 μ moles of oxygen is consumed, which is equal to about one-half of that of (A).

It is confirmed from the foregoing reaction systems (a)-1, (a)-2 and (a)-3 that the present enzyme can form hydrogen peroxide.

Quantitative determination of the generated hydrogen peroxide is made by colorimetric quantitative determination of the formed quinoneimine pigment. That is, it is confirmed by the quantitative determination of the formed hydrogen peroxide in the system of Reaction Composition A according to 4-AA method described after that 4.96 μ moles of hydrogen peroxide is formed from 5 μ moles of glycerol.

(b) Confirmation of formation of glyceraldehyde:

(b)-1. Glycerol oxidase is reacted with glycerol in the presence of oxygen, and a reaction product is identified to be glyceraldehyde.

(b)-1-1. Procedure for identification:

(b)-1-1-(1). Reaction solution:

Five drops of an aqueous solution containing 50 mg/ml of glycerol, 5 drops of solution containing 10 U/ml of glycerol oxidase in 0.02 M TES buffer solution, and 1 drop of 14,000 U/ml of catalase are collected, and reaction is carried out at 30° C. with shaking for 20 hours.

(b)-1-1-(2). Identification:

As a result of the thin layer chromatography given below (which will be hereinafter referred to as "TLC"), the product in the reaction solution is identified as glyceraldehyde by comparison with the authentic substance.

The thin layer plate used is silica gel G-60F-254 (trademark of E. Merck, West Germany), and developing solvents are solvent system 1 [butanol:acetic acid:-water=4:1:1 (by volume)], and solvent system 2 [butanol:pyridine:water=3:2:1.5 (by volume)].

After the development, three kinds of reactions, that is, p-anisidine reaction, periodic acid-benzidine reaction, and 2,4-dinitrophenylhydrazine reaction are conducted on the plate, and it is confirmed that Rf values of the reaction products and color tones of the spots formed by said reactions are identical with those of the authentic substances. The results are given in Table 2.

TABLE 2

Identification of reaction products by TLC (Rf values and coloring reaction)

| Coloring agent | Sample | | Developing solvent | |
|---|---|---|---|---|
| | | | Solvent system 1 | Solvent system 2 |
| p-anisidine hydrochloric acid reagent (1) | Glyceraldehyde (authentic substance) | Rf value | 0.67 (brown) | 0.76 (brown) |
| | Reaction product | Rf value | 0.69 (brown) | 0.78 (brown) |
| Periodic acid-benzidine reagent (2) | Glyceraldehyde (authentic substance) | Rf value | 0.66 (÷)* 0.68 | 0.76 (÷)* 0.78 |
| | Reaction product | Rf value | (÷)* | (÷)* |
| 2,4-dinitrophenyl-hydrazine reagent (3) | Glyceraldehyde (authentic substance) | Rf value | 0.67 (orange) | 0.77 (orange) |
| | Reaction product | Rf value | 0.69 (orange) | 0.78 (orange) |

Color indicated in parentheses shows color tone of the spot, and (÷)* in periodic acid-benzidine reagent means white spot in blue background.

NOTES
(1) p-anisidine hydrochloric acid reagent: reductive carbonyl compounds such as sugars react with p-anisidine hydrochloric acid to exhibit coloration characteristic of respective structures.
(2) periodic acid-benzidine reagent: polyalcohol and compounds having a similar structure thereto consume periodic acid and get to not react with benzidine reagent. Thus, those compounds are detected by a white spot.
(3) 2,4-dinitrophenylhydrazine reagent: carbonyl compound reacts with 2,4-dinitrophenylhydrazine to form 2,4-dinitrophenylhydrazone, and is detected by an orange spot.

As shown in the foregoing table, the products and the glyceraldehyde authentic substance are completely identical with one another in the Rf values and coloration by the coloring reagents. Thus, it is confirmed that the product obtained by reaction of glycerol oxidase with glycerol in the presence of oxygen is glyceraldehyde.

(b)-2. The amount of glyceraldehyde formed when glycerol oxidase is reacted with glycerol in the present of oxygen is almost equimolar to that of consumed glycerol. The fact is confirmed by adding 2,4-dinitrophenylhydrazine to the reaction system to prepare 2,4-dinitrophenylhydrazone of the product and quantitatively determining the latter product by colorimetry.

(c) Confirmation of the amount of oxygen uptake:

Consumption of oxygen in the system where glycerol oxidase is reacted with glycerol is measured by an oxygen electrode and a Warburg's manometer. As a result, it is confirmed that the amount of oxygen uptake meets with the amount of the formed glyceraldehyde.

(d) Quantitative determination of the amount of hydrogen peroxide, the amount of glyceraldehyde and the amount of oxygen uptake are carried out according to the procedures described in the above three items (a), (b) and (c). As a result, it is found that those obtained data are stoichiometrically reasonable.

It is confirmed from said qualitative and quantitative experimental results that the present enzyme oxidizes glycerol to form hydrogen peroxide and glyceraldehyde according to the following equation, that is, that the present enzyme is glycerol oxidase II.

II. Substrate specificity:

The relative activity is measured using other substrates in equimolar amounts to that of glycerol in the procedure for measuring the activity according to 4-AA method.

The relative activities on other substrates are given in Table 3, the activity on glycerol being defined as 100.

TABLE 3
Substrate specificity

| Substrate | Relative activity |
| --- | --- |
| Glycerol | 100 |
| Glycerol-3-phosphoric acid | 12 |
| Dihydroxyacetone | 293 |
| 1,2-Propanediol | 11 |
| 1,3-Propanediol | 23 |
| 1,3-Butanediol | 11 |
| 2,3-Butanediol | 16 |
| 1,4-Butanediol | 11 |
| Ethanol | 11 |
| n-Propyl alcohol | 11 |
| iso-Propyl alcohol | 23 |
| sec-Butyl alcohol | 9 |
| iso-Butyl alcohol | 14 |
| n-Butyl alcohol | 7 |

Figure 2:
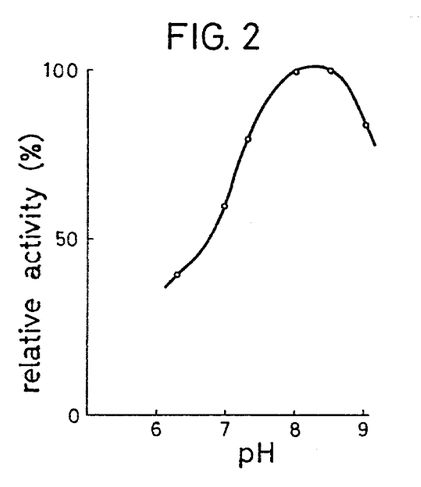
FIG. 2 shows relative activities of after incubation at 37° C. and various pH for 10 minutes.

III. Optimum pH and stable pH range:

Optimum pH is in a range of 7.8 to 8.6. The activities are measured after incubation at 37° C. for 10 minutes at various pH values, using TES buffer solutions. The results are shown in FIG. 2.

Figure 3:
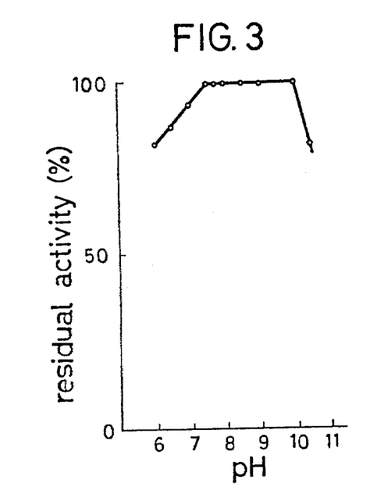
FIG. 3 shows residual activities of after treatment at 30° C. and various pH for 15 minutes.

Stable pH range is 7.5 to 10.0. Residual activities are measured after treatment at 37° C. for 15 minutes at various pH values, using TES buffer solutions. The results are shown in FIG. 3.

IV. Method for the determination of the enzyme activity:

The enzyme activity is expressed by "unit." A "unit" of the enzyme activity is defined as that amount of enzyme which will decompose 1 $\mu$ mole of glycerol at 37° C. in 1 minute in the presence of oxygen. The determination of the enzyme activity is carried out as follows: glycerol is reacted with glycerol oxidase II with stirring to form hydrogen peroxide, and 4-aminoantipyrine and phenol are reacted with the resulting hydrogen peroxide in the presence of peroxidase to derive quinoneimine pigment. The optical density in the visible portion of the resulting quinoneimine pigment is measured to determine the amount of generated hydrogen peroxide, whereby the enzyme activity is determined (which will be hereinafter referred to as "4-AA method").

In the present invention, specific activity is defined by unit per 1 mg of protein. The amount of the enzyme protein is measured according to Lowry method using copper-Folin reagent [O. H. Lowry, N. J. Rosebrough, A. L. Farr and R. J. Randall: J. Biol. Chem., 193, 265 (1951)].

(a) Principle:

Determination of the enzyme activity is carried out by reacting hydrogen peroxide generated by the enzyme with 4-aminoantipyrine and phenol in the presence of peroxidase to obtain quinoneimine pigment, and quantitatively determining the resulting quinoneimine pigment.

Reaction formulae are given by the following equations (1) and (2):

Reaction principle of equation (2) is disclosed in C. C. Allain et al.: Clin. Chem. 20, 470 (1974).

(b) Reagents:

| | | |
| --- | --- | --- |
| (1) | Substrate: aqueous 0.1M glycerol solution | 0.5 ml |
| (2) | Buffer solution: 0.1M TES buffer solution (pH 8) | 1.0 ml |
| (3) | 4-Aminoantipyrine: aqueous 2.4 mM solution | 0.5 ml |
| (4) | Phenol: 42 mM (aqueous solution) | 0.5 ml |
| (5) | Aqueous peroxidase solution: (Amount of protein: 2 mg/ml, Specific activity: 100) | 0.1 ml |
| (6) | Water | 0.3 ml |
| (7) | Aqueous enzyme solution | 0.1 ml |

(c) Operational procedure:

The reagents (1)–(6) are mixed in a test tube, and then shaken at 37° C. for 5 minutes. Then, enzyme solution is added thereto, and thus obtained mixture is made up to 3 ml with TES buffer solution. Reaction is carried out at 37° C. for 10 minutes with shaking. On the other hand, similar procedure is repeated using water in place of the test solution as a reference. The optical density of the reaction solution at 500 nm is measured, and a difference from the control is determined as $\Delta OD$ (optical density).

(d) Calculation of the enzyme activity:

One unit of glycerol oxidase II is the amount of the enzyme which will decompose 1 $\mu$ mole of glycerol at 37° C. in 1 minute.

On the other hand, the absorption coefficient of 1 mM of quinoneimine pigment is reported as 5.33 [Clin. Chem. 20, 470 (1974)], and thus, if the optical density ($\Delta OD$) at 500 nm of 3 ml of the reaction solution obtained according to the foregoing operational procedure IV-(c) is represented by a, the desired enzyme activity (A) per milliliter of the enzyme solution is calculated from the following formula:

$$A = a \times \frac{1}{5.33} \times 3 \times \frac{1}{10}$$

$$= a \times 0.56 \text{ (unit/ml)}$$

Figure 4:
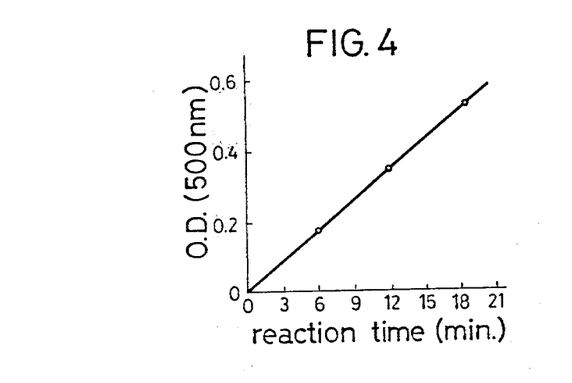
FIG. 4 shows relation between reaction time and OD value (at 500 nm) in measuring the activity of the enzyme.

OD values at 500 nm of reaction solutions are measured by changing the reaction time in the measurement of the enzyme activity, and the results shown in FIG. 4 are obtained.

It is evident from FIG. 4 that the OD values at 500 nm are proportional to the reaction times.

V. Optimum temperature range for action

Figure 5:
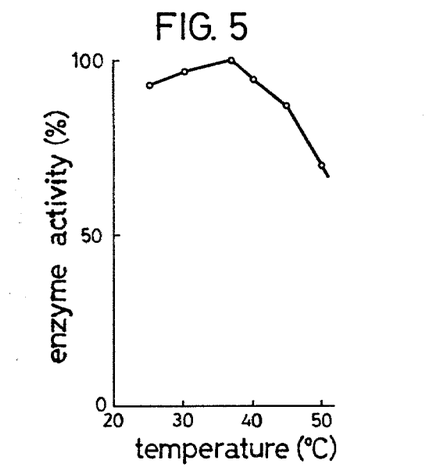
FIG. 5 shows the enzyme activities of after incubation at pH 8 and various temperature for 10 minutes.

The enzyme activities after incubation at pH 8 and various temperatures for 10 minutes are shown in FIG. 5. The optimum temperature is at about 37° C.

Figure 6:
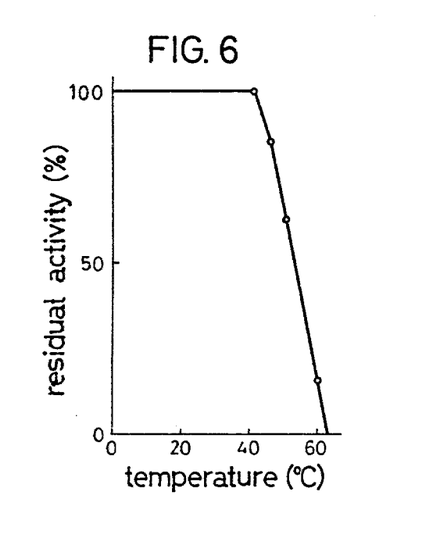
FIG. 6 shows residual activities of after treatment at various temperatures for 15 minutes.

VI. Inactivation conditions by pH, temperature, etc:
  o Inactivation by pH condition:

As described in the foregoing item III on the optimum pH and stable pH range, the enzyme is inactivated below pH 7.0 or above pH 10.5.

o Inactivation by temperature:

Residual activity is measured after heat treatment at pH 7.8 for 15 minutes in 0.1 M TES buffer solution. As the results are shown in FIG. 6, the enzyme is 100% stable up to 40° C., but is about 15% inactivated at 45° C.

VII. Inhibition, activation and stabilization

As described above.

VIII. Substrate affinity

Michaelis constant* (Km value) against substrate (glycerol) produced by the genus Penicillium is $8.0 \times 10^{-3}$ M. On the other hand, Km values of glycerol oxidase I (U.S. application Ser. No. 897,695 filed on Apr. 19, 1978) of *Aspergillus japonicus* and *Neurospora crassa* discovered previously are $1.85 \times 10^{-2}$ M and $1.90 \times 10^{-2}$ M, respectively and Km value of the genus Penicillium is below half as compared with those of the genus Aspergillus and Neurospora.

*Determination of Michaelis constant is described in the following reference. H. Lineweaver and D. Burk, J. Amer. Chem. Soc., 56, 658 (1934).

Accordingly, glycerol oxidase of the genus Penicillium has a high affinity against glycerol and it turned out that the glycerol oxidase is further appropriate to determine glycerol.

Glycerol oxidase II provided by the present invention is preferably applied as a method for the quantitative determination of glycerol. The methods are described below.

(a) A method which comprises reacting glycerol oxidase II with glycerol in the presence of oxygen, and quantitatively determining the formed hydrogen peroxide.

(b) A method which comprises reacting glyceraldehyde which is formed in the above (a) with 2, 4-dinitrophenylhydrazine, forming 2, 4-dinitrophenylhydrazone, quantitatively determining the 2, 4-dinitrophenylhydrazone by colorimetry, and thereby quantitatively determining glycerol.

(c) A method which comprises reacting glycerol oxidase II with glycerol in the presence of oxygen, and measuring an amount of oxygen uptake of the system.

The principles and the procedures of the methods (a), (b) and (c) are described in the above item I. However, as an example, the method (a) for the quantitative determination of glycerol by measuring the amount of the formed hydrogen peroxide will be described below:

The optical density of reaction solutions at 500 nm is determined according to the operational procedure described in the foregoing item IV-(c), using solutions containing 0.1 mg of the enzyme having a specific activity of 2.4 per milliliter of the solutions changing the concentration of the substrate (glycerol) solution to 0.1 mM, 0.2 mM, 0.5 mM, 1.0 mM, 5.0 mM, and 10.0 mM in the foregoing item IV-(c). The results are shown in Table 4.

TABLE 4

| Substrate concentration | 0.1mM | 0.2mM | 0.5mM | 1.0mM | 5.0mM | 10.0mM |
|---|---|---|---|---|---|---|
| OD value at 500 nm | 0.058 | 0.116 | 0.301 | 0.598 | 2.995 | 5.990 |

It is observed that there is a linear relationship between the substrate concentration (glycerol concentration) and the OD value of reaction solutions at 500 nm. On the basis of this principle, glycerol contained in solution at an unknown concentration can be quantitatively determined.

Thus, the glycerol concentration of a solution can be measured using glycerol oxidase II. This fact will suggest a new procedure and kit for the quantitative determination of glycerol.

A method for the quantitative determination of glycerol has been in demand, for example, in the field of biochemistry. Various methods are known for the quantitative determination of triglyceride by hydrolyzing triglyceride in serum to form glycerol and fatty acid, and measuring the glycerol.

As the chemical method for the quantitative determination of glycerol, chromotropic acid method, acetylacetone method, triazole method, Randrup method, and Mendelsohn fluorescense method are known, but all those methods have such a disadvantage that the reactions in those methods are non-specific to glycerol.

As the enzyme method, a method using glycerokinase (E. C. 2.7.1.30) is known, but the reaction must be conducted together with pyruvate kinase (E. C. 2.7.1.40) and lactate dehydrogenase (E. C. 1.1.1.27), and thus it takes much time in the measurement and consequently the method is unsuitable for the treatment of a large number of samples.

It has been found that the present glycerol oxidase II directly oxidizes glycerol to form hydrogen peroxide stoichiometrically. Thus, the obtained hydrogen peroxide is easily converted to a coloring system, and quantitative determination of glycerol, that is, quantitative determination of triglyceride can be very simple and specifically made by the colorimetrical quantitative determination.

As is apparent from the foregoing description, it is obvious that the present glycerol oxidase II of the genus Penicillium has the same action as glycerol oxidase I of the genus Aspergillus or the genus Neurospora discovered previously, but has other characteristic properties in optimum pH, substrate specificity, etc.

Further, it turned out that the present glycerol oxidase II has properties of heat-resistance and low Km value and is suitable enzyme for the quantitative determination.

Now, the present invention will be described in detail below.

EXAMPLE 1

Penicillium sp. KY 868 (FERM-P 4567, NRRL 11339) is inoculated in 300 ml of seed medium containing 30 g/l of glycerol, 6 g/l of corn steep liquor and 2 g/l of yeast extract (pH 6.5 before sterilization) in a 2-l Erlenmeyer flask, and cultured at 25° C. with shaking for 48 hours.

Nine hundred milliliters (corresponding to three flasks) of the resulting speed culture is inoculated in 15l of the same medium as said seed medium in a 30-l jar fermenter, and cultured at 25° C. with aeration (15 l/min.) and stirring (250 rpm) for 40 hours. After the culturing, the resulting culture broth is filtered through a Buchner funnel, and the cakes are washed with water, whereby about 73 g (dry basis) of microbial cells is obtained.

The microbial cells are suspended in 5 l of 10 mM TES buffer solution (pH 7.8), and disrupted in Dyno-mill (made by Willy A. Bachofen, Switzerland). After the disruption, the disrupted suspension is centrifuged by a freezing centrifuge (20,000×G for 20 minutes), and 4.5 l of supernatant (protein content; 23 g, specific activity: 0.01 unit/mg) is obtained. The resulting supernatant is admixed with ammonium sulfate, and fractions precipitated at 30–70% saturation with ammonium sulfate are collected, and dissolved in 50 ml of 10 mM TES buffer solution (pH 7.8). The resulting solution is dialyzed against 10 l of 10 mM TES buffer solution, using a cellophane tube as a dialysis membrane.

Dialysis is continued for 48 hours with total of 40 l of dialysis solution, while exchanging the dialysis solution at every 12 hours. Dialyzed enzyme solution is passed through a column (5.5×40 cm) of DEAE cellulose (made by Serva Co., West Germany) equilibrated in advance with 10 mM TES buffer solution (pH 7.8). Enzyme is adsorbed through said operation, and unadsorbed impure protein is washed out with the same buffer. Then, the elution is carried out by 2 l of 0.01 M TES buffer (pH 7.8) containing 0.1 M NaCl, whereby glycerol oxidase is eluted. Five hundred milliliters of the active fractions (protein content: 0.6 g, specific activity 0.21) are collected, and admixed with ammonium sulfate to make 70% saturation and to precipitate the enzyme.

Then, precipitates are collected by centrifugation (20,000×G for 20 minutes), and dissolved in 23 ml of 10 mM TES buffer solution (pH 7.8). The solution is passed through a column (5.5×80 cm) of Sephadex G-100 (made by Pharmacia Fine Chemicals, Co., Sweden) equilibrated in advance with 10 mM TES buffer solution (pH 7.8). One liter of 10 mM TES buffer solution (pH 7.8) is passed through the column and eluate is obtained in fractions. From the fractions, 300 ml of a fraction having a high specific activity (protein content: 140 mg, specific activity: 0.61) is obtained, and admixed with ammonium sulfate to make 70% saturation and to precipitate enzyme. Then, the precipitates are collected by centrifugation (20,000×G for 20 minutes) and dissolved in 10 ml of 10 mM TES buffer solution (pH 7.8). The resulting solution is dialyzed for 24 hours against 5 l of 10 mM TES buffer solution (pH 7.8), using a cellophane tube as a dialysis membrane, while twice exchanging the dialysis solution. After the dialysis, the resulting enzyme solution is passed through a column (5.5×20 cm) of hydroxyapatite equilibrated in advance with 10 mM TES buffer solution (pH 7.8). Furthermore, 250 ml of the same buffer is passed through the column, and eluate is obtained in fractions. Fractions having a high specific activity are collected, and freeze-dried, whereby 4.9 mg of purified powdery enzyme preparate of glycerol oxidase II (specific activity: 6.3) is obtained. The purified enzyme has a specific activity about 630 times as high as that of cell extract. The yield is 11.4 in terms of activity.

EXAMPLE 2

(a) Reagents to be used:

| | | |
|---|---|---|
| (1) | Test solution: aqueous glycerol solution (concentration: unknown) | 0.5 ml |
| (2) | Buffer solution: 0.1M TES buffer solution (pH 8) | 1.0 ml |
| (3) | 4-aminoantipyrine: aqueous 2.4 mM solution | 0.5 ml |
| (4) | Phenol: aqueous 42 mM solution | 0.5 ml |
| (5) | Peroxidase: aqueous peroxidase solution (protein content: 20 mg/ml, specific activity: 1000) | 0.1 ml |
| (6) | Water | 0.3 ml |
| (7) | Enzyme: (protein content: 1.0 mg/ml, specific activity: 2.4) | 0.1 ml |

(b) Procedure:

The above reagents (1)–(6) are placed in a test tube, and shaken sufficiently at 37° C. for 5 minutes. Then, an enzyme solution is added thereto, and thus obtained reaction mixture is made up to 3 ml with TES buffer solution. Reaction is conducted at 37° C. for 10 minutes with shaking.

On the other hand, similar procedure is repeated using water in place of the test solution as a reference.

Figure 7:
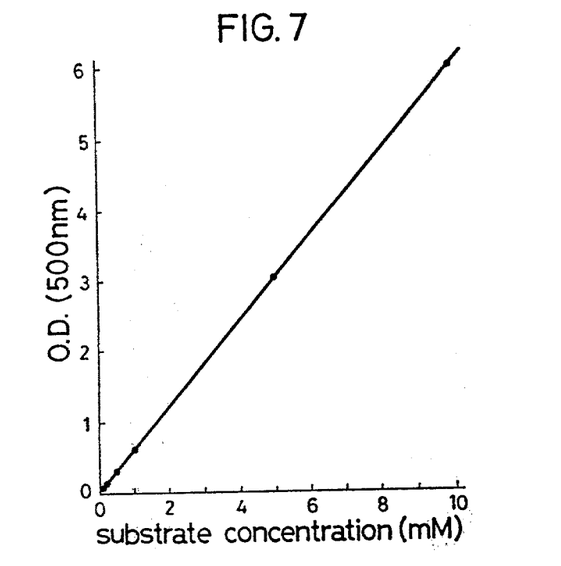
FIG. 7 is graphical representation of Table 4.

The OD value at 500 nm of the test solution is measured, and a difference $\Delta OD$ from the reference is 0.322. From the working curve of FIG. 7, glycerol content in the test solution is determined to be 0.532 mM.

We claim:

1. An oxidizing enzyme of glycerol having the following properties:
   (1) action: oxidizes glycerol in the presence of oxygen to form hydrogen peroxide and glyceraldehyde;
   (2) substrate specificity: a specific activity for glycerol and dihydroxyacetone;
   (3) optimum pH: 7.8–8.6;
   (4) stable pH: 7.5–10.0;
   (5) optimum temperature for action: 37° C.; and
   (6) Michaelis constant against glycerol (Km value): $8.0 \times 10^{-3}$ M.

2. The oxidizing enzyme of claim 1 wherein said enzyme is produced by culturing of a microorganism belong to the genus Pencillium.

3. The oxidizing enzyme of claim 2 wherein said microorganism is Penicillium sp KY 868 (FERM-P 4567, NRRL 11339).

4. The oxidizing enzyme of claim 1 wherein said enzyme has a molecular weight of 300,000 or more.

5. A process for producing an oxidizing enzyme of glycerol that oxidizes glycerol in the presence of oxygen to form hydrogen peroxide and glyceraldehyde which comprises culturing a microorganism having the ability to produce said enzyme and belonging to the genus Penicillium in a nutrient medium and recovering the enzyme from the resulting culture broth.

6. The process of claim 5, wherein the nutrient medium has a pH of from 6 to 8 at the start of culturing and culturing is carried out at a temperature of from 18° to 40° C., during agitation for a period of from 30 to 72 hours.

7. The process of claim 5, wherein the microorganism is Pencillium sp KY 868 (FERM-P 4567, NRRL 11339).

* * * * *